United States Patent
MacDougald et al.

(10) Patent No.: US 6,648,645 B1
(45) Date of Patent: Nov. 18, 2003

(54) METHOD FOR MANUFACTURING DENTAL RESTORATIONS

(75) Inventors: Joseph A. MacDougald, Madison, CT (US); Carlino Panzera, Bellemead, NJ (US); Weitao Jia, Wallingford, CT (US); Dmitri Brodkin, West Orange, NJ (US); Martin L. Schulman, Orange, CT (US); Paul Panzera, Mt. Holly, NJ (US); Bruce Alpert, Madison, CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 187 days.

(21) Appl. No.: 09/653,377

(22) Filed: Sep. 1, 2000

Related U.S. Application Data

(60) Provisional application No. 60/188,490, filed on Mar. 10, 2000, and provisional application No. 60/152,264, filed on Sep. 2, 1999.

(51) Int. Cl.⁷ .............................. A61C 5/10
(52) U.S. Cl. ........................ 433/223; 433/212.1
(58) Field of Search .................... 433/218, 219, 433/223, 212.1; 264/19

(56) References Cited

U.S. PATENT DOCUMENTS

| | | |
|---|---|---|
| 4,265,669 A | 5/1981 | Starling |
| 4,585,417 A | 4/1986 | Sozio |
| 4,689,197 A | 8/1987 | Groll |

(List continued on next page.)

FOREIGN PATENT DOCUMENTS

| | | |
|---|---|---|
| DE | 198 20 763 A1 | 9/1997 |
| EP | 0 328 772 | 8/1989 |
| EP | 523019 | 1/1993 |
| EP | 0 872 218 A2 | 10/1998 |
| JP | 60032706 A * | 2/1985 |
| WO | WO 94/08783 | 4/1994 |
| WO | WO 01/15620 A1 * | 8/2001 |

OTHER PUBLICATIONS

Dae–Joo Kim and Myung–Hyun Lee, Mechanical Properties of Tape–Cast Alumina–Glass Dental Composites. J. Am. Ceram Soc. 82[11]3167–72 (1999).

Kappert, H.F, Knode, H., In–Ceram: Testing a new ceramic material. Quintessence, vol. 16, 87–97, 1993.

*Primary Examiner*—Ralph A. Lewis
(74) *Attorney, Agent, or Firm*—Ann M. Knab

(57) ABSTRACT

A ceramic tape is provided in its green state so that it is malleable and formable to a mold for forming a dental restoration, but will not break or crack as it is applied to the mold. Pressure may be applied to further form or adapt the ceramic tape to the shape of the mold. Heat is applied simultaneously with pressure or in a separate step to achieve high density and strength in the ceramic material. A vacuum atmosphere may be used with the application of pressure and/or heat. One or more layers of surface material such as porcelain or composite resin may be applied to the ceramic to form the dental restoration. The process is useful in the manufacture of dental materials or restorations including but not limited to orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors.

Also provided is a ceramic powder in combination with one or more media materials to form a homogeneous mixture. The mixture may then be used to form a dental restoration as is or may be used to form feedstock such as filaments or wires which are then used to fabricate a dental restoration. The filaments or wires may be used in a fused deposition-modeling machine to build dental restorative materials by computer aided design software.

11 Claims, 3 Drawing Sheets

U.S. PATENT DOCUMENTS

| | | |
|---|---|---|
| 4,798,536 A | 1/1989 | Katz |
| 4,828,495 A | 5/1989 | Bell |
| 4,879,136 A | 11/1989 | Polz |
| 4,957,440 A | 9/1990 | Hankins |
| 4,980,124 A | 12/1990 | Dimmer |
| 5,080,589 A | 1/1992 | Oden |
| 5,104,591 A | 4/1992 | Masuhara |
| 5,121,329 A | 6/1992 | Crump |
| 5,336,091 A * | 8/1994 | Shoher et al. ............... 433/215 |
| 5,346,397 A | 9/1994 | Braiman |
| 5,653,791 A | 8/1997 | Panzera |
| 5,711,833 A | 1/1998 | Apte et al. |
| 5,714,025 A | 2/1998 | Brungardt |
| 5,776,382 A * | 7/1998 | Kim et al. .................... 264/16 |
| 5,779,833 A | 7/1998 | Cawley et al. |
| 5,788,498 A | 8/1998 | Wohlwend |
| 5,839,900 A | 11/1998 | Billet |
| 5,866,058 A | 2/1999 | Batchelder |
| 5,900,207 A | 5/1999 | Danforth |
| 5,910,273 A | 6/1999 | Thiel |
| 5,916,498 A | 6/1999 | Hofmann |
| 5,942,063 A | 8/1999 | Mori |
| 5,958,468 A | 9/1999 | Kunkel |
| 5,975,905 A | 11/1999 | Kim |

\* cited by examiner

METHOD FOR MANUFACTURING DENTAL RESTORATIONS

CROSS-REFERENCE TO RELATED APPLICATIONS

This application claims priority to U.S. Provisional Application No. 60/152,264, filed Sep. 2, 1999, and U.S. Provisional Application No. 60/188,490, filed Mar. 10, 2000 which are incorporated herein by reference.

FIELD OF THE INVENTION

The present invention relates generally to a method for manufacturing dental restorations such as dental crowns and dental bridges and more specifically to a method of manufacturing dental restorations using high strength ceramic materials.

BACKGROUND OF THE INVENTION

Strength and reliability are important factors to consider when manufacturing dental restorations. Dental restorations must be able to withstand the normal mastication forces and stresses that exist within an oral environment. Different stresses are observed during mastication of different types of food, which can be experimentally measured by placing, for example, a strain gauge in inlays on the tooth. Stresses differ depending not only on the type of food, but also on the individual. For example, stress values may range from 570 to 2300 lb/inch$^2$ for a single chewing thrust on a piece of meat and from 950 to 2400 lb/inch$^2$ for a single thrust on a biscuit. The physical properties of dental restorations must be adequate to withstand the stresses applied by the repetitive forces of mastication.

Ceramic materials have proven to be reliable in the fabrication of single unit dental restorations. U.S. Pat. No. 4,798,536 to Katz, U.S. Pat. No. 5,653,791 to Panzera et al., and an article by Kabbert and Knode entitled "Inceram: Testing a New Ceramic Material", Vol.4, pp 87–97 (1993) each disclose ceramic compositions having leucite therein to provide strength and reliability to dental restorations. The strength of the materials is in the area of 170 MPa which is much higher than that of conventional porcelain which exhibits strengths of about 70 MPa. Nevertheless, the strength and/or toughness values of the aforementioned ceramic materials may not be adequate for the fabrication of multiple unit restorations.

Due to the unique shape and size of dental restorations, it is often difficult to achieve uniform physical properties which are effective in dental restorations. Moreover, fabrication techniques often involve manual blending of powders, liquids and dispersants which may not provide the optimal homogeneity for the mixture. This may result in uneven shrinkage and poor mechanical properties in the finally sintered restoration. The standard deviation of mechanical properties is very high for manually blended mixtures and the products produced therefrom are inconsistent in properties. Furthermore, nonuniform particle size may lead to porosity that will result in weak structures.

U.S. Pat. Nos. 4,265,669, 4,585,417 and 5,975,905 are directed to the fabrication of dental restorations using ceramic powders in combination with binders and are hereby incorporated by reference. U.S. Pat. No. 4,265,669 to Starling, et al. disclose dry flowable ceramic powder mixtures containing about 10–15% of a silicone resin. The mixtures are shaped and sized as desired and sintered to monolithic structures without any shrinkage or distortion occurring during firing. The mixture is required to be soft at about 30° C. and hardens at about 150° C. As a result, a complicated molding transfer process must be performed. Additionally, the firing process for the structures is lengthy, typically as long as ten hours or more which reduces the chances for an efficient and facile operation. Similarly, U.S. Pat. No. 4,585,417 to Sozio, et al. involves a complicated process. The firing time required for the process is very long, requiring a minimum of two stages over a period of twelve hours, which is impractical for many dental laboratories.

There is a need to provide high strength, ceramic restorations having structural integrity and reliability and optimum bonding properties. It is desirable to produce high strength ceramic restorations that are compatible with a wide range of cost-effective ceramic materials. It is beneficial to provide dental restorations having uniform physical properties throughout the restoration and to simplify the process of manufacturing dental restorations to provide a more user-friendly process.

SUMMARY OF THE INVENTION

These and other objects and advantages are accomplished by the process herein comprising applying one or more strips of ceramic tape or ribbon to a mold for a dental restoration. The ceramic tape is in its green state so that it is malleable and formable to the mold, but does not break or crack as it is applied to the mold. Pressure may be applied to further form or adapt the ceramic tape to the shape of the mold. Heat is applied simultaneously with pressure or in a separate step to achieve high density and strength in the ceramic material. A vacuum atmosphere may be used with the application of pressure and/or heat. One or more layers of surface material such as porcelain may be applied to the ceramic to form the dental restoration. The process is useful in the manufacture of dental materials or restorations including but not limited to orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors.

In another embodiment herein, ceramic powder and one or more media materials are combined to form a homogeneous mixture. The mixture may then be used to form a dental restoration as is or may be used to form feedstock such as filaments or wires which are then used to fabricate a dental restoration. The filaments or wires may be used in a fused deposition-modeling machine to build dental restorative materials by computer aided design (CAD) software. The restorative materials include but are not limited to an orthodontic appliance, bridge, space maintainer, tooth replacement appliance, splint, crown, partial crown, denture, post, tooth, jacket, inlay, onlay, facing, veneer, facet, implant, abutment, cylinder, and connector.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figure 1:
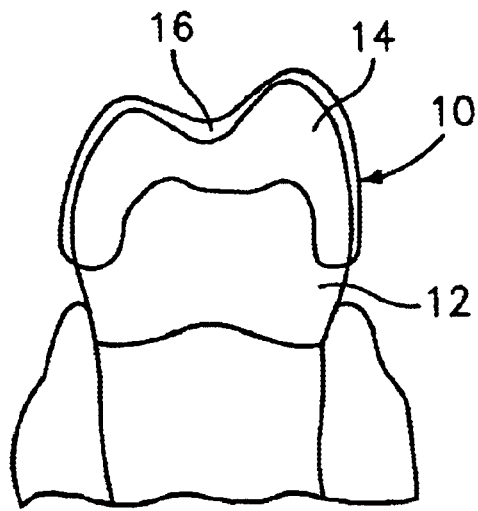
FIG. 1 is a sectional view of a tooth with a crown thereon formed in accordance with the invention.

As will be appreciated, the present invention provides a process of manufacturing dental materials and restorations using powders of ceramic material in the green state provided in the form of a putty or tape. The putty or tape is easily malleable and can be readily applied to a die to form the desired shape. FIG. 1 shows a dental restoration 10 made in accordance herein fitted on a natural tooth stump 12 that has been prepared by the dentist by removing enough of the tooth structure to allow proper thickness of the final crown. Dental restoration 10 comprises a core 14 that was fabricated from ceramic tape applied to a die and sintered. Thereafter, a coating 16 is formed on core 14 by applying porcelain material and sintering or by applying a composite material and thereafter curing the material.

Figure 2:
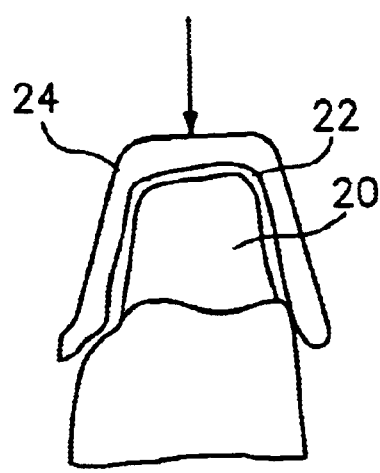
FIG. 2 is a sectional view of a crown being manufactured in accordance with the invention.

The manufacture of dental restorations typically involves the preparation of a die of the prepared tooth. This is done in a known manner, preferably with a stone cast. FIG. 2 shows a die 20 that is used to create a crown such as dental restoration 10 shown in FIG. 1. In accordance with one embodiment herein, one or more pieces, strips or ribbons of ceramic tape 22 is placed or wrapped on or over die 20 and conformed to the shape of die 20. The conforming step generally involves folding and/or trimming tape 22 followed by any suitable swaging type operation or adaptation. The swaging operation may include but is not limited to hammering, bending, wrapping, shaping and pressing, by application of pressure to the tape by hand or with the use of utensils or pressing equipment such as an isostatic, hot or cold pressing machine. In FIG. 2, pressure is applied to a permeable membrane 24 by a press (not shown). Permeable membrane 24 assists in maintaining the ceramic material on the die.

Tape 22 is fabricated of a ceramic material such as alumina, zirconia, mullite, spinel, porcelain, titania, lithium disilicate, leucite, amorphous glass, lithium phosphate, and combinations thereof, or any high strength ceramic material that can withstand the stresses created in the mouth. One important aspect herein is that the particles of powder used to fabricate the tape preferably are in the shape of spheres to provide good particle packing. This results in little or no porosity in the sintered product. Alternatively, the particles may be of uniform particle size to achieve good particle packing. The size of the particles is in the range of about 0.5 to about 50 microns and preferably in the range of about 1 to about 3 microns for crystalline ceramics such as alumina and from about 5 to about 20 microns for glass-ceramics such as lithium silicate-based glass ceramics.

The tape used herein may be formed by a variety of known processes including, but not limited to, tape casting, extrusion, calendaring, partial pultrusion with a support member, and roll compaction or using the doctor blade method as set forth in U.S. Pat. No. 5,975,905 which is hereby incorporated by reference. Each of the methods involves combining ceramic powders with one or more forms of media to carry the ceramic powders. Medium (media) is defined herein as a fluid suspension component surrounding the ceramic powder that either forms inorganic compounds or evaporates during processing. The media have a viscosity of at least 1000 cps, and preferably at least 10,000 cps. Examples of useful media herein include materials that are thermoplastic, thermosetting, water soluble, or organic-solvent soluble such as ethylene or polyethylene glycol, methacrylate resins, wax, water, polyvinyl alcohol (PVA), polyvinyl butyral (PVB), and similar binder-type materials known in the art. One commercially available wax is Plastodent U, available from Degussa, Germany. Preferably, the media materials are any suitable vehicles that will vaporize upon heat treatment without leaving a residue. The media may include but are not limited to materials in the art that are known as binders, plasticizers, dispersing agents, solvents and mixtures thereof.

The ceramic powder and medium or media are mixed and formed into a thin, flat sheet in its green state. It is preferable that the ceramic powder or particulate is present in an amount of about thirty to about ninety percent by weight, and the medium or media is/are present in an amount of about ten to about seventy percent by weight of the mixture. More preferably, the particulate is present in an amount of about fifty to about eighty-five percent by weight, and the media are present in an amount of about fifteen to about fifty percent by weight of the mixture. Most preferably, the particulate is present in an amount of about seventy to about eighty percent by weight, and the media are present in an amount of about twenty to about thirty percent by weight of the mixture.

In one embodiment, the medium is composed substantially or entirely of wax, with the remainder, if any, of an organic or hydrocarbon compound to control the malleability of the ceramic material. It is preferable that the binder remains flexible during the forming operation.

In a preferred embodiment, the medium comprises a polymeric material with minimal content of carbon, which, upon heating the ceramic/medium material, will minimize the potential for carbon black residue to affect the shade of the final ceramic restoration. This is of paramount importance since esthetic properties of the dental restoration must accurately match the properties of the existing teeth in a person's mouth. In this embodiment, the medium is preferred to be a material from the silicone polymer family with a minimum of about 50% of SiO content, which will vaporize partially upon heat treatment and also leave white natural colored silica which is essentially a basic ingredient of the ceramic material. The preferred medium is composed substantially or entirely of silicone polymers, with the remainder, if any, of a volatile organic solvent to facilitate the blending/mixing of the powder and medium into a dough-like paste or putty initially. The use of silicone polymers or a mixture of silicone polymers containing at least fifty percent of an SiO group oxide in combination with ceramic powders produces a workable dough-like consistency. The viscosity of the silicone polymer is at least 1,000 cps and preferably at least about 10,000 cps. Examples of silicone polymers include vinyl terminated polydimethylsiloxane, hydroxy terminated polydimethyl siloxane, and polydimethyl siloxane. Examples of commercially available silicone polymers include Baysilone U Basic Compounds, HS-N Gum, V60K, Fluid W1000 (all from GE), and Polymer VQM 800 and Polymer VS series (both from Hanse Chemie).

The tape is used in its green state so that it may easily and readily form to the shape of the die upon which it is placed. The thickness of the tape will vary between about 0.1 to about 2 mm and preferably between about 0.2 to about 1 mm. One or more layers of tape may be used to form the dental restorative product. The layers may be fired after each layer has been applied in separate firing cycles, or alternatively, all layers may be fired in one firing cycle after all layers have been applied. The layers of tape may be comprised of the same material or of a different material. For example, the first layer may comprises a tape of higher fusing material than the second layer of tape. As another example, the first layer may be ceramic and the second layer may be a glass or a glass-ceramic or the same or a different ceramic.

After the tape has been sufficiently placed onto a die of desired configuration, it is heated to effect high density and strength in the ceramic. Alternatively, pressure or vacuum, and heat may be applied simultaneously. The heating process may involve a burnout cycle whereby the organic additives (i.e., the media) are removed partly or completely by thermal decomposition. This cycle varies depending upon the material used but typically ranges from about 300 to about 1000° C. and more preferably from about 400 to about 800° C. The firing time may vary for a time ranging from about ten (10) seconds to about twelve (12) hours, more preferably for a time ranging from about one (1) minute about five (5) hours and most preferably for a time ranging from about ten (10) minutes to about one (1) hour and may be performed in air, nitrogen, argon or similar atmosphere. Sintering may be carried out at about 600° to about 1400° C. for about one (1) minute to about twelve (12) hours to full density and more preferably for about one (1) hour to about five (5) hours and most preferably less than about three (3) hours to produce a dental restorative material such as a ceramic core that is ready or nearly ready to receive veneering porcelain or similar coating. The full heating process which may include a burnout cycle with a sintering cycle, or a sintering cycle only, is preferably from about ten (10) minutes to about five (5) hours and more preferably from about one (1) hour to about four (4) hours, and most preferably less than about three (3) hours.

If silicone polymers are utilized, the heating process for the silcone polymers is preferably in the range of about ten (10) seconds to about two (2) hours and more preferably in the range of about one (1) minute to about one (1) hour and in the temperature range of from about 300 to about 1000° C. and the sintering process is preferably in the range of from about one (1) minute to about one (1) hour in the temperature range of from about 600° to about 400° C. so that the entire heating process is less than about three hours.

The die should have a coefficient of thermal expansion that matches that of the ceramic material being used to assure acceptable fit of the final restoration. After sintering, the reasonably soft die is removed, for example, by sand blasting. Alternatively, after sintering the first core layer, subsequent layers of various ceramic/porcelain materials such as commercially available OPC® 3G™ porcelain available from Jeneric/Pentron Inc., Wallingford, Conn. can be fired on the core which remains on the same die. As a further option, composite resin materials such as commercially available Sculpture®, Sculpture® Flow, both available from Jeneric/Pentron Inc., Wallingford, Conn. and ArtGlass available from Kulzer, Germany, can be applied to first core material, and thereafter cured.

If the ceramic powder is a higher strength ceramic such as alumina or zirconia, sintering may be carried out in one step in a high temperature furnace at about 1200° to about 1800° C. for about 2 to about 10 hours when the die being used is oversized proportionally to the amount of shrinkage of the ceramic. Alternatively, sintering may be carried out in two steps whereby the shaped article is sintered to partial density at about 1000° to about 1200° C. and consequently infiltrated with a porcelain or glass material as described in U.S. Pat. No. 5,910,273, which is hereby incorporated by reference.

With the exception of silicone media, the burnout cycle is preferably performed slowly so as to burn off or decompose the organics without introducing cracks or blisters into the material. It is preferable that the burnout cycle is performed in air, nitrogen, argon or similar atmosphere and that sintering is carried out in a vacuum atmosphere.

The process herein may be used to manufacture a variety of dental restorations wherein the ceramic tape is used to form a core or support shell for the restoration. During the firing of the ceramic tape, the medium is partially or completely removed and some shrinkage occurs. Shrinkage is comparable to that encountered using conventional ceramic forming operations. To compensate for shrinkage, the dimensions should be prescaled to the desired size. Approximately, 15% shrinkage of the uncured ceramic tape is expected during post-process densification, depending upon the specific tape formulation. The fired ceramic will have a flexural strength in the range of about 200 to about 1200 MPa depending upon the material used. For example, the flexural strength of alumina ranges from about 200 to about 600 MPa. The flexural strength of zirconia ranges from about 530 to about 1200 MPa.

Figure 3:
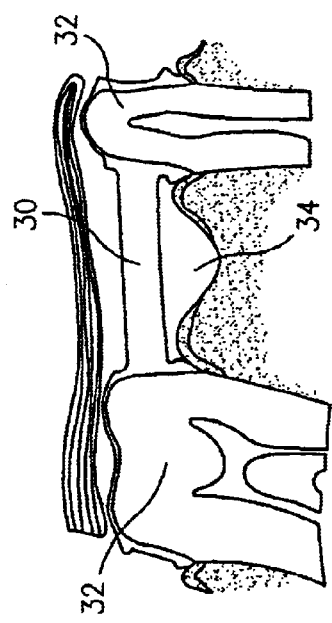
FIG. 3 is a sectional view of an occlusal support manufactured in accordance with the invention.
Figure 4:
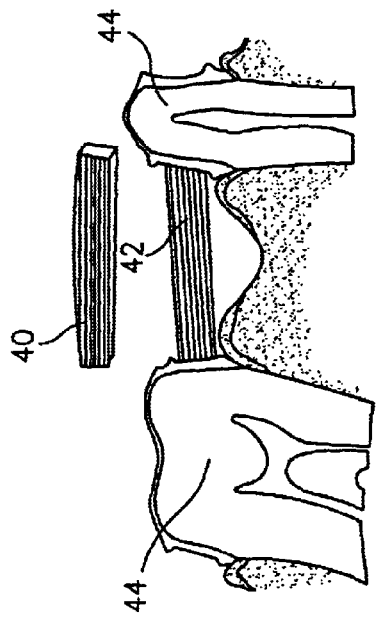
FIG. 4 is a sectional view of buccal and lingual bars manufactured in accordance with the invention.
Figure 5:
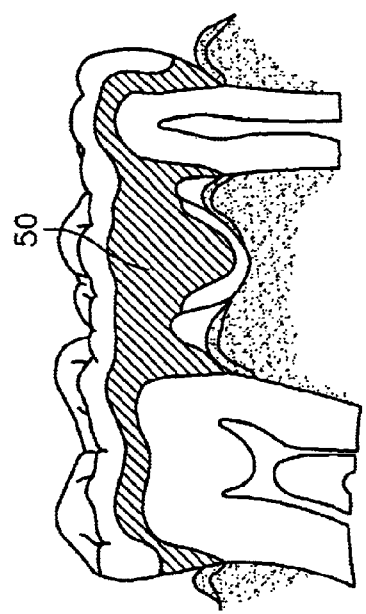
FIG. 5 is a sectional view of a bridge manufactured in accordance with the invention.
Figure 6:
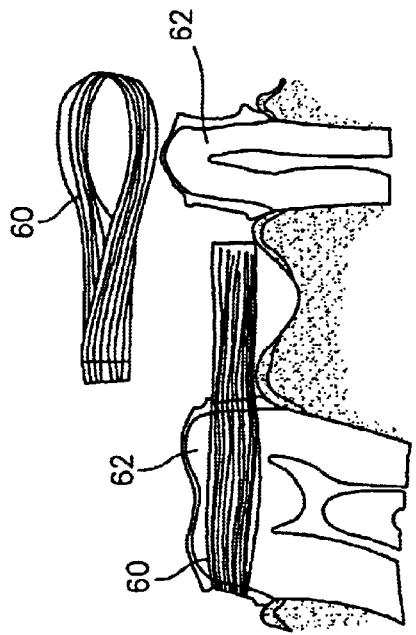
FIG. 6 is a sectional view showing loops of tape in the manufacture of a bridge in accordance with the invention.

FIGS. 3 through 6 show uses of the materials manufactured in accordance with the invention. In FIG. 3, ceramic tape may be applied in layers to form a support structure 30 that extends over abutments 32 and across a gap 34. FIG. 4 shows bars 40 and 42 which may be manufactured from ceramic tape and inserted between abutments 44. FIG. 5 shows a pontic 50 formed from layers of ceramic tape. FIG. 6 illustrates ceramic tape 60 being wrapped around abutments 62 to form a support structure for a bridge. In the various illustrations, ceramic tape, in its green state, is applied to the molds or dies shown, to conform to the shape of the mold and is thereafter fired to achieve optimum density and strength. Dental restorative materials including, but not limited to orthodontic appliances, bridges, space maintainers, tooth replacement appliances, splints, crowns, partial crowns, dentures, posts, teeth, jackets, inlays, onlays, facings, veneers, facets, implants, abutments, cylinders, and connectors may be fabricated using the materials and processes described herein.

In another embodiment herein, ceramic powder and one or more media materials, as defined above, are combined to form a homogeneous mixture. The same powders and media materials described above in the tape embodiment may be used herein to form a homogeneous mixture that results in a putty-like consistency. Preferably, the homogeneity of the mixture is achieved by combining the components in a mixer having a heated mixing chamber such as that available from Charles Ross & Son Company, Hauppauge, N.Y. It is important that the ceramic powder or particulate is well dispersed in the medium to achieve homogeneity throughout the mixture because the final properties of the sintered restoration are affected by the rheology of the particulate and medium mixture. The particulate, as used herein, refers to powders, platelets, granules, whiskers, and discontinuous and continuous fibers. It is preferable that the particles of powder used herein be spherical in shape to provide good particle packing. This results in little or no porosity in the sintered product. Alternatively, the particles may be of uniform particle size to achieve good particle packing. The particles range in size from about 0.5 to about 50 microns and preferably in the range of about 1 to about 3 microns for crystalline ceramics such as $Al_2O_3$ and from about 5 to about 20 microns for glass-ceramics such as lithium silicate.

It is preferable that the ceramic powder or particulate is present in an amount of about thirty to about ninety percent by weight, and the medium or media is/are present in an amount of about ten to about seventy percent by weight of the total mixture. More preferably, the particulate is present in an amount of about fifty to about eighty-five percent by weight, and the media are present in an amount of about fifteen to about fifty percent by weight of the mixture. Most preferably, the particulate is present in an amount of about seventy to about eighty percent by weight, and the media are present in an amount of about twenty to about thirty percent by weight of the mixture. If the particulate/binder mixture is not homogeneous throughout, the sintered restoration formed from such a mixture may shrink nonuniformly and exhibit poor mechanical properties. The restoration may fracture under normal stresses encountered in the mouth. The particulate/binder mixture and process of manufacture described herein reduce and/or prevent the possibility of fracture of the sintered restoration by providing a homogeneous starting mixture. The standard deviation of the mechanical properties in the resulting restoration is narrow in comparison to those exhibited in dental restorations fabricated by other processes, such as with dental restorations made from components which are manually blended. Preferably, the standard deviation of the mechanical properties in the restorations made by the process herein is about 15 to about 20 percent of the mean or average standard deviation, or more preferably about 10 to about 15 percent of the mean or average standard deviation.

The mixture may be supplied in containers such as syringes, cartridges, jars and the like, and can be used to fabricate restorations manually or by machine. The putty mixture is applied to a die and formed by hand or by machine, with or without the application of pressure, to mold the mixture to the shape of the die. Thereafter, the die with the mixture thereon is fired at times and temperatures listed above for the tape embodiment.

Alternatively, the mixture may be used to form feedstock such as filaments or wires that are then used to fabricate a dental restoration. The filaments or wires may be used in a fused deposition-modeling machine to build dental restorative materials by computer aided design (CAD) software. It is important that the particulate/media includes a dispersing agent to enhance the dispersion of the particles within the media system and improve the flow of the feedstock composition during molding. Dispersing agents include used fatty glycerol esters, fatty bisamides, and fatty esters not based upon glycerin.

Figure 7:
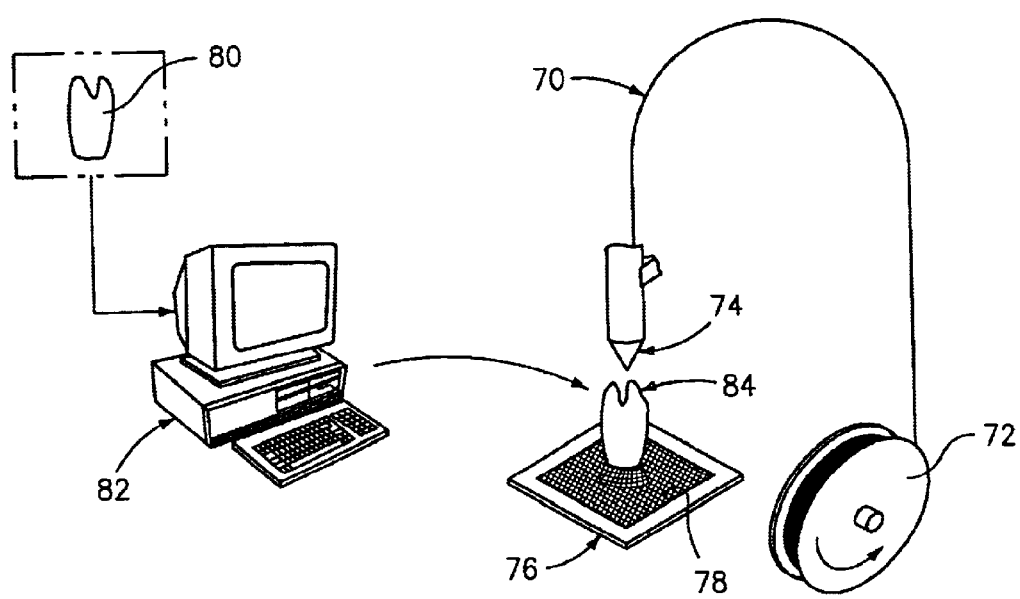
FIG. 7 is a diagrammatic view showing the fused deposition forming step in accordance with the invention.

Reference is made to FIG. 7 that shows the forming process of a fused deposition-modeling machine. Commercially available FDM®2000 rapid prototyping system from Stratasys Inc., Minneapolis, Minn. is one such fused deposition modeling machine which may be used in the process herein. Filament 70 is shown on a supply spool 72. Filament 70 is formed from one or more ceramic, glass, or glass-ceramic powders in combination with one or more media additives including, but not limited to binders, plasticizers and like additives. Filament 70 is fed to a dispensing head 74 of a dispensing machine (not shown) which is positioned proximate a build platform 76. Platform 76 includes a substrate 78 upon which a dental restorative material may be built. Platform 76 and dispensing head 74 may both move relative to one another. The shape of the restoration to be built is dictated by the design 80 generated by the computer program in computer 82. The restoration 84 which is to be built, may be built in layers. Preferably, filament 70 is heated in dispensing head 74 to a fluid state and is dispensed at a controlled flow rate onto substrate 78. It is important that substrate 78 be fabricated of a material, such as wire mesh sandpaper or a water-soluble wax, which minimizes localized shrinkage and permits easy release of the formed article therefrom. The material in dispensing head 74 may be deposited layer by layer onto substrate 78. It is preferable that the layers are thin, e.g., in the range of about 0.0005 to about 0.01 inch in thickness and most preferably about 0.001 inch in thickness. Thinner layers provide a smoother finished surface of the resulting restoration. The layers may take any shape as dictated by the computer program. It is preferable that each layer is solidified prior to the deposition of the next layer. Preferably, each layer is dispensed in a fluid state, solidifies and adheres to the previous layer, thereby providing a strong bond between layers. U.S. Pat. Nos. 5,900,207 and 5,121,329 are directed to fused deposition forming processes and are hereby incorporated by reference.

The fused deposition process may be arranged so that multiple and different feedstock materials can be dispensed either alternately or through multiple dispensing nozzles. Following formation by the fused deposition process, restoration 84 may be further processed to improve the surface finish. Such processing may include machining of the surface by sanding, grinding, vibrating in an abrasive media, and other techniques known in the art. This machining step may take place in the green state prior to binder removal, and thus, prior to full densification, after densification, or at a combination of these stages. Also, a machining step may be performed on a layer-by-layer basis during the fused deposition forming process. Restoration 84 may be further subjected to a post fabrication treatment such as cold isostatic pressing or hot isostatic pressing to facilitate the removal of any residual internal voids, delaminations or other defects. Furthermore, the restoration in its green state may be processed to remove the binder or a portion therefrom by, for example, solvent extraction, supercritical fluid processes, thermal processes and combinations thereof. A densification step may follow the binder removal step. This may be conducted by thermal treatment (e.g., sintering), hot pressing, hot isostatic pressing, reaction bonding, directed metal oxidation, reaction infiltration, chemical vapor deposition and combinations thereof.

The restorative materials fabricated herein may include but are not limited to an orthodontic appliance, bridge, space maintainer, tooth replacement appliance, splint, crown, partial crown, denture, post, tooth, jacket, inlay, onlay, facing, veneer, facet, implant, abutment, cylinder, and connector.

The following examples illustrate the practice of the invention.

EXAMPLE 1

Seventy five grams of Synspar® Dentin D2 shade porcelain powder were blended with twenty five grams of a silicone polymer mixture having seventy parts of a vinyl terminated dimethylsiloxane gum (BAYSILONE polymer HS-N, GE) and thirty parts of an SiH terminated silane. The paste formed had a putty consistency, was non-sticky and very soft and workable. The material was loaded in a dental restorative syringe and was ready for use in the fabrication of a dental restoration.

EXAMPLE 2

A paste was prepared as in Example 1. Using a clean glass slab, the paste was flattened into a sheet in thickness of about 0.7 mm on the glass slab. The sheet was cut into tape-like strips. The strips were applied to a stone die to form a dental restoration. The tape was shaped and adapted on the die. The die and tape thereon were sintered in a dental porcelain furnace (JP1200® furnace available from Jeneric/Pentron Inc., Wallingford, Conn.) at a heating rate of about 50° C./minute to 970° C. and held at 970° C. for about one minute. The finished Synspar® porcelain coping was dense and porosity free and exhibited the desired shade.

EXAMPLE 3

Eleven grams of 3G™ OPC® ceramic powder were mixed with six grams of a polymer mixture of five parts of silicone gum and 1 part of silicone oil. The mixture exhibited a dough-like consistency. The dough-like mixture was flattened into thin sheets and applied onto a refractory die forming a coping. The die and coping were heated at a rate of about 30° C./minute to about 890° C. in a dental porcelain furnace and held for about one minute. After sintering, the die and coping were removed from the furnace and cooled to room temperature. The finished porcelain coping was dense and free of porosity.

EXAMPLE 4

A coping was made as in Example 3 above. A second layer of material comprising 3G™ OPC® porcelain was applied to the finished core using a pressing furnace (AutoPress® Plus furnace available from Jeneric/Pentron Inc., Wallingford, Conn.) and sintered at a heating rate of 42° C./minute to 760° C. and with no hold time. The finished OPC® 3G™ OPC® porcelain coping was dense and free of porosity.

EXAMPLE 5

A core was made as in Example 3 above using 3G™ OPC® ceramic powder and a polymer mixture of five parts of silicone gum and one part of silicone oil. The surface of the ceramic core was then sandblasted with 50 $\mu$m of Al2O3 particles under 85 psi pressure and etched for one minute with 9% HF acid gel (available form Jeneric/Pentron Inc.). The etched core surface was water rinsed cleaned and air-dried. After brushing on a layer of Silane Coupling Agent (available form Jeneric/Pentron Inc.) to the prepared core surface, a layer of Sculpture Flow™ A2 shade resin composite material (available from Jeneric/Pentron Inc.) was injected from the syringe and coated onto the silanated ceramic core surface to form the final anatomy of a tooth restoration and then cured in a Cure-Lite Plus™ (available form Jeneric/Pentron Inc.) visible light cure unit for two minutes. The combination of a ceramic core with a dental resin composite fives desirable properties and esthetics to a dental restoration.

EXAMPLE 6

3G™ OPC® ceramic powder was mixed with vinyl-modified polydimethylsiloxane V-60K (available form Osi Specialites, Inc., Greenwich, Conn.). The powder load was 72 wt %. The resulting mixture had a consistency of dough and is easily rolled into tape or shaped manually on a die. Copings were built using the dough applied onto refractory die made from Polyvest Refractory Die Material (available from Whip Mix Corp, Louisville, Ky.) and fired at 890° C. and held at this temperature for 1 minute. The copings were reasonably dense.

As will be appreciated, the present invention provides a simple and effective method for producing high strength ceramic restorations. While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A process for fabricating a dental material comprising:

mixing ceramic powder and one or more media together to achieve homogeneity throughout the mixture and to form a putty;

applying the putty to a model to conform to the shape of the model and to form a ceramic core material; and sintering the model with the putty thereon for a time of less than about three hours to provide a dental ceramic core material.

2. The process of claim 1 wherein the dental ceramic core material is highly dense.

3. The process of claim 1 wherein the dental ceramic core material comprises mechanical properties having a low standard deviation.

4. The process of claim 1 wherein the ceramic powder comprises a glass-ceramic, a glass powder, a ceramic powder or mixtures thereof.

5. The process of claim 1 wherein the ceramic powder comprises a material selected from alumina, zirconia, mullite, spinel, porcelain, titania, lithium disilicate, leucite, amorphous glass, lithium phosphate, and mixtures thereof.

6. The process of claim 1 wherein the dental ceramic core material is an orthodontic appliance, bridge, space maintainer, tooth replacement appliance, splint, crown, partial crown, denture, post, tooth, jacket, inlay, onlay, facing, veneer, facet, implant, abutment, cylinder, or connector.

7. A process for fabricating a dental material comprising:

applying a putty to a model to conform to the shape of the model and to form a ceramic core material, whereby the putty comprises ceramic powder and one or more media having homogeneity throughout the putty; and sintering the model with the putty thereon for a time of less than about three hours to provide a dental ceramic core material.

8. The process of claim 7 further comprising applying a layer of material selected from the group consisting of glass, ceramic, and glass-ceramic on the sintered dental ceramic core material and sintering the layer of material to the dental ceramic core material.

9. The process of claim 7 further comprising applying a layer of composite resin material on the sintered dental ceramic core material and curing the layer of composite resin material to the dental material.

10. A process for fabricating a dental material comprising:

mixing ceramic powder and one or more media together to achieve homogeneity throughout the mixture and to form a putty;

applying the putty to a model to conform to the shape of the model and to form a ceramic core material; and sintering the model with the putty thereon for a time in the range of about one minute to about five hours to provide a dental material.

11. The process of claim 1 wherein the sintering time is in the range of ten minutes to one hour.

\* \* \* \* \*